United States Patent
Yamamoto et al.

(10) Patent No.: US 6,979,552 B2
(45) Date of Patent: Dec. 27, 2005

(54) METHOD OF LIPID ASSAY AND REAGENT FOR USE THEREIN

(75) Inventors: Mitsuaki Yamamoto, Ibaraki (JP);
Shoko Yamamoto, Ibaraki (JP);
Mitsuhiro Nakamura, Ibaraki (JP);
Kazunori Saito, Ibaraki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 10/416,166

(22) PCT Filed: Nov. 13, 2001

(86) PCT No.: PCT/JP01/09899

§ 371 (c)(1),
(2), (4) Date: May 14, 2003

(87) PCT Pub. No.: WO02/40707

PCT Pub. Date: May 23, 2002

(65) Prior Publication Data

US 2004/0053350 A1 Mar. 18, 2004

(30) Foreign Application Priority Data

Nov. 14, 2000 (JP) ............... 2000-346791

(51) Int. Cl.$^7$ ............ C12Q 1/60; C12Q 1/00; C12Q 1/34; C12Q 1/26; C12Q 1/28; G01N 33/92
(52) U.S. Cl. ............ 435/11; 435/4; 435/18; 435/25; 435/28; 436/71
(58) Field of Search ............ 435/28, 6, 11, 975, 435/18, 25, 4; 436/71

(56) References Cited

U.S. PATENT DOCUMENTS

| | | | |
|---|---|---|---|
| 4,689,309 A | 8/1987 | Jones | |
| 4,826,761 A | 5/1989 | Arai et al. | |
| 5,166,051 A | 11/1992 | Killeen et al. | |
| 6,143,514 A | * 11/2000 | Ullman et al. | ........... 435/28 |

FOREIGN PATENT DOCUMENTS

| | | |
|---|---|---|
| EP | 0 259 076 | 8/1987 |
| EP | 1020532 | 7/2000 |
| JP | 56-155853 | 12/1981 |
| JP | 62-82357 | 4/1987 |
| JP | 6-16720 | 3/1994 |
| JP | 6-242110 | 9/1994 |
| JP | 9-299 | 1/1997 |
| JP | 2600065 | 4/1997 |
| JP | 9-121895 | 5/1997 |
| JP | 2653755 | 9/1997 |
| JP | 2799835 | 9/1998 |
| JP | 11-56395 | 3/1999 |
| JP | 2000-116400 | 4/2000 |
| JP | 2000-325097 | 11/2000 |
| WO | 99/10526 | 3/1999 |
| WO | 00/78999 | 12/2000 |

OTHER PUBLICATIONS

M.D. Marazuela et al.: "Free cholesterol fiber-optic biosensor for serum samples with simplex optimization" Biosensors & Bioelectronics, vol. 12, No. 3, pp. 233-240 1997.

* cited by examiner

*Primary Examiner*—Kent Bell
(74) *Attorney, Agent, or Firm*—Oblon, Spivak, McClelland, Maier & Neustadt, P.C.

(57) ABSTRACT

A method of lipid assay characterized by assaying the lipids contained in a blood component in the presence of an organic silicon compound. The method can cause specific conditions for direct methods while satisfying requirements such as no influence on precision of assay, no burden on assay apparatus, and easy availability.

4 Claims, 3 Drawing Sheets

METHOD OF LIPID ASSAY AND REAGENT FOR USE THEREIN

FIELD OF THE INVENTION

The present invention relates to a method of separately saying lipid components in specific lipoprotein fractions efficiently by a simple procedure using a small amount of sample the present invention also relates to a reagent used for the method.

DESCRIPTION OF BACKGROUND ART

Cholesterols, triglycerides, and phospholipids which are major lipids in the living body are combined with apoproteins to form lipoproteins in blood. The lipoproteins are grouped into chylomicron, very low density lipoprotein (VLDL), low density lipoprotein (LDL), high density lipoprotein (HDL), and the like according to their physical properties. Among these lipoproteins, it is known that LDL is a causative factor for arteriosclerosis, whereas HDL exhibits an anti-arteriosclerosis effect.

Total cholesterols and total triglycerides in blood have been assayed for the purpose of preventing ischemic heart diseases or evaluating the effects of treatments for such diseases. Epidemiological studies have proved that the cholesterol level in LDL has a positive correlation with the frequency of arteriosclerosis occurrence, whereas the cholesterol level in HDL has a negative correlation with the frequency of arteriosclerosis occurrence. Importance of knowing fluctuations in each lipoprotein fraction such as LDL and HDL has been understood. Nowadays, apoprotein B and apoprotein A-I, which are protein components forming each lipoprotein, or cholesterol in each lipoprotein fraction is assayed.

As mentioned above, as the method of assaying lipids components in blood, a method of determining the total amount of specific lipid contained in all lipoproteins such as total cholesterol and total triglycerides and a method of determining cholesterols in specific lipoproteins such as LDL, HDL, and the like can be given.

Of these, the former method is based on the combination of an enzyme for the lipid component to be assayed and conditions enabling the reaction of the lipid component with the enzyme without regard to the type of lipoproteins (for example, a surfactant with low lipoprotein selectivity such as Triton X-100). The method enables assaying the lipid components to be assayed in all lipoproteins.

The latter method, on the other hand, is based on the combination of an enzyme for the lipid component to be assayed and specific conditions enabling the enzyme to react only with the lipid component to be assayed in specific lipoproteins. The method enables the assay of the lipid components to be assayed in the specific lipoprotein fractions.

These specific conditions have been conventionally established by a method of isolating the lipoproteins to be assayed from a sample by ultra centrifugation, electrophoresis, gel filtration, precipitation using a precipitation agent (precipitation method), or the like (the method is hereinafter referred to as "fractionation method").

In recent years, a number of methods for establishing specific conditions without using the fractionation method (hereinafter referred to as "direct methods") have been developed. Such methods include a method of utilizing the different reaction times of bile acid for each lipoprotein fraction in the determination of HDL cholesterols (Japanese Patent Publication No. 016720/1994), a method of reacting the lipoproteins to be assayed with an enzyme under the condition that the lipoproteins not to be assayed stay aggregated (Japanese Patent Application Laid-open Publication No. 242110/1994), a method of using a sugar compound (Japanese Patent No. 2653755), a method of using a modification enzyme (Japanese Patent No. 2600065), a method of using a surfactant which does not dissolve lipoproteins (Japanese Patent No. 2799835), a method of removing cholesterols in lipoproteins not to be assayed by a previous enzyme reaction (Japanese Patent Application Laid-open Publication No. 000299/1997), a method of using carrageenan (Japanese Patent Application Laid-open Publication No. 121895/1997), a method of using a surfactant having lipoprotein selectivity (Japanese Patent Application Laid-open Publication No. 056395/1999), a method of using Calixarene (WO 98/59068), and a method of using a phosphorus compound (Japanese Patent Application Laid-open Publication No. 116400/2000).

Some of these direct methods are used in practice in daily clinical tests due to their simple procedures as compared with the precipitation method involving complicated procedures. However, even the direct methods which have been put into practice have problems. For example, the method of adding a precipitation agent to the reagent has problems: interference of the aggregates on assay precision and a damage to measuring equipment such as clogged flow passages with the products produced from reaction of the precipitation agent with an alkaline detergent for washing measuring equipment. As for a method of using a modification enzyme, there are problems such as process control in enzyme modification procedures (quality control) and cost increase.

Accordingly, an object of the present invention is to provide a method of assaying lipid components in blood and the like using a substance capable of establishing the specific conditions under the direct method while neither affecting assay precision nor damaging assay instruments, and also satisfying other conditions such as easy availability.

DISCLOSURE OF THE INVENTION

The inventors of the present invention have conducted extensive studies to achieve the above object and completed the present invention with the following method. As for assaying the lipid components in specific lipoproteins to be assayed such as HDL cholesterols, the HDL cholesterols alone can be selectively assayed with specificity even in the absence of precipitation agents and modification enzymes if an organic silicon compound is added to the reagent, and the enzyme having the cholesterol as a substrate is mixed with the sample to be assayed.

Specifically, the present invention provides a method of lipid assay characterized by the assay conducted in the presence of an organic silicon compound and a reagent used for the assay.

DETAILED DESCRIPTION OF THE INVENTION AND PREFERRED EMBODIMENTS

Figure 1:
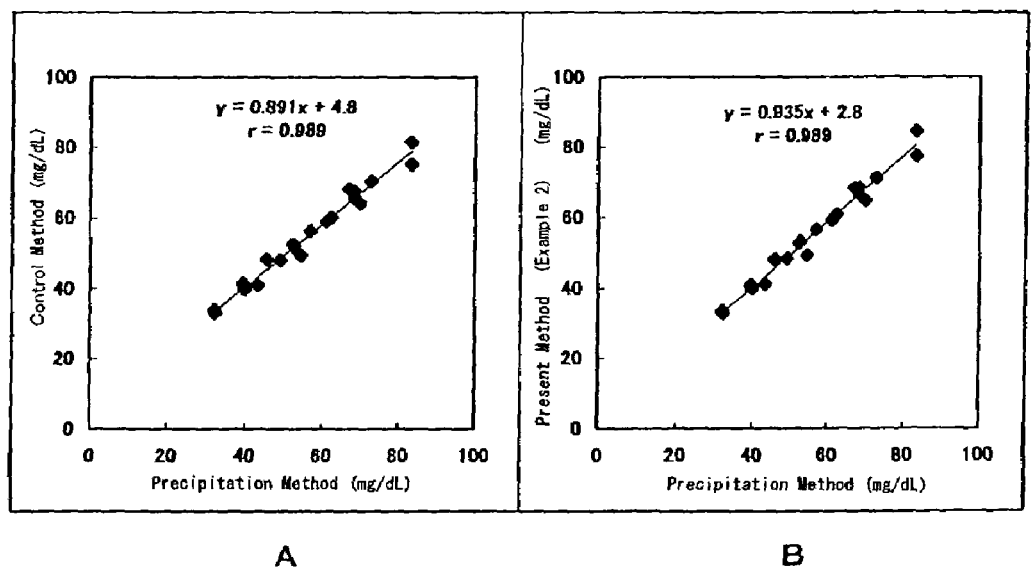
FIG. 1 is a chart for showing the correlation between the results of assaying HDL cholesterol in a blood serum sample obtained by the method of the present invention shown in Example 2 or the control method using a reagent not containing an organic silicon compound of the present invention and the results obtained by the precipitation method, wherein A shows the correlation for the control method and B shows the correlation for the method of the present invention.

The method of the present invention comprises assaying lipid using a known reagent for assaying lipids in the presence of an organic silicon compound.

Silicones and their derivatives can be given as the organic silicon compound in the present invention. The silicones are the polymers which have organic groups such as an alkyl group or aryl group. The polymers comprise —(Si—O)$_n$—, which is generally called polysiloxane, the recurrence structure of siloxane unit which consists of a silicon atom bonded with an oxygen atom. Properties of silicones differ according to the molecular structure. Viscosity, volatility, and other properties vary according to the degree of polymerization, types of side chains, the degree of crosslinking, and the like. There are liquid silicones, greasy silicones, rubbery silicones, and resinous silicones. These silicones and their derivatives are commercially available under classification names of silicone, high polymerization silicone, cyclic silicone, alkyl silicone, silicone-containing surfactant, modified silicone oil, and the like. The modified silicone oil is the silicone oil to which an organic group is added. According to the added organic group, the modified silicone oil is classified as an amino modified silicone oil, epoxy modified silicone oil, carboxyl modified silicone oil, polyether modified silicone oil, alkyl modified silicone oil, or the like. According to the structure, the modified silicone oil is classified as a side chain silicone oil, both terminal silicone oil, one terminal silicone oil, and side chain both-terminal silicone oil. These silicones and derivatives may be used either individually or in combination of two or more in achieving the object of the present invention. Manufacturers publish catalogues describing properties and the like of their organic silicon products. Specific organic silicon compounds to be used may be selected by referring to these catalogues.

In measuring the target lipid, the organic silicon compound of the present invention may be either added simultaneously with the sample and the reagent for assaying the target lipid or mixed with the sample before adding the reagent for assaying the target lipid. Alternatively, the target lipid may be assayed by first preparing a mixture of the sample and a part of the reagent for assaying the target lipid and adding to the mixture the remaining portion of the reagent containing the organic silicon compound of the present invention.

There are no specific limitations to the method of detecting the target lipid after the addition of the reagent for assaying the target lipid. For example, spectrophotometric analysis using a combination of a peroxidase and a chromogen and a method of directly detecting a coenzyme and hydrogen peroxide can be given.

The amount of the organic silicon compound used for the sample in the present invention varies according to the type of the lipid to be assayed, the properties of the sample, the type of the reagent used, the presence or absence of the later-described surfactant or glycerol, or the amount of the surfactant or glycerol, and the like. Although optimum conditions should be selected by experiment, generally used amount of the organic silicon compound is about 0.0001–5 mass % (hereinafter simply referred to as "%"), and more preferably about 0.001–5%.

It is preferable to apply the above-described direct method to the present invention, that is, it is preferable to use the organic silicon compound of the present invention in combination with the reagent for the direct method. When used in combination with a surfactant which does not dissolve lipoproteins (Japanese Patent No. 2799835) or a surfactant having lipoprotein selectivity (Japanese Patent Application Laid-open Publication No. 056395/1999), for example, the organic silicon compound of the present invention can enhance the properties of these surfactants.

In addition, it is possible to emulsify the organic silicon compound of the present invention by adding a surfactant, glycerol, and the like to adjust the water solubility.

As the surfactant, any of anionic surfactants, nonionic surfactants, cationic surfactants, and ampholytic surfactants may be used without specific limitations. Examples include alkyl ether carboxylates, salts of N-acylamino acid, alkyl phosphates, N-acyl taurates, sulfonates, alkyl sulfates, polyoxyethylene alkyl ether sulfates, acetic acid betaines, imidazolines, alkyl ammonium salts, amide amines, polyhydric alcohol fatty acid esters, alkyl glyceryl ethers and their fatty acid esters, propylene glycol fatty acid esters, glycerides, polyglycerides, polyoxyethylene glycerides, sorbitan fatty acid esters, polyoxysorbitan fatty acid esters, polyoxyethylene sorbit fatty acid esters, polyoxyethylene lanolins, polyoxyethylene lanolin alcohols, polyoxyethylene bees wax derivatives, polyoxyethylene castor oil, polyoxyethylene hydrogenated castor oil, polyoxyethylene sterols, polyoxyethylene hydrogenated sterols, polyethylene glycol fatty acid esters, polyoxyethylene alkyl ethers, polyoxyethylene polyoxypropylene alkyl ethers, polyoxyethylene polyoxypropylene condensates of ethylenediamine, polyoxyethylene alkylphenyl ethers, polyoxyethylene alkyl amines, sucrose fatty acid esters, polyoxyethylene fatty acid amides, polyoxyethylene alkylphenyl formaldehyde condensates, polyoxyethylene alkyl ether phosphoric acid, salts of polyoxyethylene alkyl ether phosphoric acid, and the like.

These surfactants may be added to the assay system either individually or in combination of two or more. The combination and amount of these surfactants vary according to the type of silicones and their derivatives, the type of surfactant used, and the like. Although optimum conditions should be selected by experiment, generally used concentration of the surfactant in the assay system is about 0.0001–5%, and more preferably about 0.001–5%.

In addition to the surfactant, polymer emulsifying agents such as an acrylic acid-alkyl methacrylate copolymer and carboxy vinyl polymer, organic solvents such as ethanol, silicones and their derivatives not adversely affecting the assay specificity, and the like can be used in adjusting the water solubility.

The lipid to be assayed by the method of the present invention may be any lipid present in the living body, and particularly preferable lipids are those forming lipoproteins such as cholesterols, triglycerides, and phospholipids.

Any enzyme having the target lipid as the substrate can be used in assaying the lipid in the method of the present invention. Enzymes commonly used for assaying cholesterols, triglycerides, and phospholipids described in outline of Clinical Diagnosis Method, the 30$^{th}$ edition, (Kanehara and Co., Ltd., 1993), for example, can be used in the present invention and are included in the scope of the present invention.

When cholesterols are assayed among these lipids, enzymes commonly used for assaying cholesterols such as cholesterol dehydrogenase, cholesterol oxidase, and cholesterol esterase can be used without a limitation. These enzymes may be those originating from microorganisms, animals, or plants or may be those prepared by a genetic engineering technique. Either chemically modified or unmodified enzymes can be used.

These enzymes may be optionally used in combination with a coenzyme, a detecting enzyme or dyeing agent, or the like. As the coenzyme, nicotine amide adenine dinucleotide and the like can be given. As the detecting enzyme, peroxidase and the like can be given. As the dyeing agent, Trinder reagent, aminoantipyrine, and the like can be given.

The detecting enzymes may be used either individually or in combination of two or more. The amount used differs according to the enzymes. Although not specifically limited, the enzyme in the amount of 0.001–100 unit/mL, and preferably 0.1–100 unit/mL, is used.

The method of the present invention can be advantageously carried out by using a reagent for assaying lipid prepared by appropriately formulating the above-described organic silicon compound, enzyme for assaying lipid, dyeing agent, coenzyme, and the like. As required, reagents having affinity with specific lipoproteins, including other enzymes such as catalase, salts, pH adjusting buffering agents, surfactants, antiseptic agents, proteins such as albumin, antibodies, antibiotics, saponins, lectins, and polyanions, can be added to the extent that the assay specificity is not adversely affected and the specific lipoproteins are not aggregated.

As the buffering agent, any buffering agent such as Good's buffer, phosphoric acid, Tris buffer, and phthalate may be used inasmuch as the buffering agent can establish buffering conditions of pH of the reaction solution in the range of 4–10. Although not specifically limited, the amount in the range of 0.0005–2 mol/L, and preferably of 0.01–1 mol/L, is applicable. In practice, optimum conditions should be selected by experiment in due consideration to the properties of the enzyme used, other components contained in the reagent, and the like.

Specific examples of the reagent for assaying lipid for advantageously carrying out the method of the present invention are given below.

(HDL-Cholesterol Assay Reagent)
(1) Organic silicon compound
(2) Cholesterol esterase
(3) Cholesterol oxidase
(4) Peroxidase
(5) Dyeing agent (4-aminoantipyrine and disulfobutyl metatoluidine, etc.)
  A surfactant having lipoprotein selectivity and other additives may be optionally added.

(LDL-Cholesterol Assay Reagent)
  (First Reagent)
(1) Organic silicon compound
(2) Cholesterol esterase
(3) Cholesterol oxidase
(4) Peroxidase
(5) Either one of two compounds generating a color by combination (e.g. 4-aminoantipyrine)
  A surfactant having lipoprotein selectivity and other additives may be optionally added.
  (Second Reagent)
(6) The other of two compounds generating a color by combination (e.g. disulfobutylmetatoluidine)
(7) Surfactant with low lipoprotein selectivity

EXAMPLES

The present invention will be described in more detail by way of Examples which should not be construed as limiting the present invention.

Example 1

The effect of the present invention was confirmed using HDL and LDL fractions prepared by ultracentrifugation as the samples. The reagent with the following formulation was used for assaying cholesterols in the HDL and LDL fractions.

| (First reagent) | |
|---|---|
| PIPES buffer solution (pH 6.5) | 50 mmol/L |
| 4-Aminoantipyrine | 0.5 mmol/L |
| (Second reagent) | |
| PIPES buffer solution (pH 6.5) | 50 mmol/L |
| Cholesterol esterase | 1 unit/mL |
| Cholesterol oxidase | 1 unit/mL |
| Disulfobutylmetatoluidine | 1.0 mmol/L |
| Peroxidase | 5 unit/mL |
| Organic silicon compound (all manufactured by Nippon Unicar Co., Ltd.) | 1% |

Hitachi 7170 automatic analyzer was used. 240 μL of the first reagent was added to 2.4 μL of the sample. Five minutes later, 80 μL of the second reagent was added. Absorbance at a wavelength of 600 nm was measured immediately before the addition of the second reagent and 5 minutes thereafter. The difference of the two measurements was regarded as the absorbance of the sample. As a control, a reagent which contains 1% Triton X-100 having low lipoprotein selectivity instead of the organic silicon compound of the present invention was used as the second reagent.

Relative sample absorbances measured using reagents containing a different organic silicon compound for each as the second reagents were determined assuming the absorbance of the sample using the second reagent containing the Triton X-100 as 100. The ratio of the relative sample absorbance for LDL to the relative sample absorbance for HDL was calculated. The results are shown in Table 1.

TABLE 1

| Added components | Relative absorbance for HDL | Relative absorbance for LDL | Ratio of relative absorbance (LDL/HDL) |
|---|---|---|---|
| Organic silicon compound 1 (NUC-silicone L7002) | 23 | 1 | 0.04 |
| Organic silicon compound 2 (NUC-silicone L7604) | 94 | 9 | 0.10 |
| Organic silicon compound 3 (NUC-silicone FZ2118) | 49 | 15 | 0.31 |
| Organic silicon compound 4 (NUC-silicone FZ2162) | 14 | 7 | 0.50 |
| Organic silicon compound 5 (NUC-silicone FZ2163) | 49 | 16 | 0.33 |
| Surfactant (Triton X-100) | 100 | 100 | 1.00 |

The LDL/HDL ratio of the relative absorbance when measured by using the second reagents containing the organic silicon compounds of the present invention was in the range of 0.04–0.5. The results indicate that the organic silicon compound of the present invention established special conditions under which the reaction between cholesterols in HDL and enzymes is predominant over the reaction between cholesterols in LDL and enzymes.

Example 2

The effect of the present invention was confirmed using 20 serum samples containing lipoproteins. Reagents with the following formulation were used for assaying.

| (First reagent) | |
|---|---|
| Bis-Tris buffer solution (pH 6.0) | 50 mmol/L |
| Cholesterol oxidase | 1 unit/mL |
| Peroxidase | 1.25 unit/mL |
| Disulfobutylmetatoluidine | 0.5 mmol/L |
| Flufenamic acid | 150 μmol/L |
| (Second reagent) | |
| Bis-Tris buffer solution (pH 6) | 50 mmol/L |
| Cholesterol esterase (Asahi Kasei Corporation) | 1.5 unit/mL |
| 4-Aminoantipyrine | 1.0 mmol/L |
| Emulgen B-66 | 1.5% |
| Organic silicon compound (NUC-Silicon L720 manufactured by Nippon Unicar Co., Ltd.) | 0.001% |

Hitachi 7170 automatic analyzer was used. 240 μL of the first reagent was added to 2.4 μL of the sample. Five minutes later, 80 μL ot the second reagent was added. Absorbance at 600 nm wavelength was measured immediately before the addition of the second reagent and 5 minutes after the addition of the second reagent, to determine the HDL cholesterol concentration from the difference in the absorbance values (Two point method) A control serum with a known concentration was used as a calibration substance. As a control, a reagent not containing the organic silicon compound of the present invention was used as the second reagent.

At the same time, the HDL cholesterol concentration in the serum sample was determined using a commercially available precipitation reagent kit (HDL-C·2 kit manufactured by Daiichi Pure Chemicals Co., Ltd.). The correlation coefficients and regression formula were compared, taking the value of the reagent in the precipitation method as X axis and the measured value in Examples as Y axis. The results are shown in Table 2 and FIG. 1.

TABLE 2

| Sample | Precipitation method | Control | Method of the present invention |
|---|---|---|---|
| 1 | 83.2 | 81.4 | 84.4 |
| 2 | 83.2 | 75.2 | 77.4 |
| 3 | 72.7 | 70.4 | 71.3 |
| 4 | 69.8 | 64.0 | 64.7 |
| 5 | 68.1 | 67.6 | 68.3 |
| 6 | 68.3 | 65.5 | 66.3 |
| 7 | 62.3 | 60.0 | 60.8 |
| 8 | 61.1 | 59.0 | 59.1 |
| 9 | 56.9 | 56.2 | 56.5 |
| 10 | 54.4 | 49.3 | 49.2 |
| 11 | 52.7 | 51.8 | 53.2 |
| 12 | 52.3 | 52.5 | 52.6 |
| 13 | 49.0 | 48.0 | 48.4 |
| 14 | 45.6 | 48.1 | 48.1 |
| 15 | 43.3 | 40.9 | 41.1 |
| 16 | 39.8 | 39.8 | 39.9 |
| 17 | 39.5 | 41.3 | 40.7 |
| 18 | 32.3 | 33.0 | 32.7 |
| 19 | 32.2 | 33.8 | 33.5 |
| 20 | 66.9 | 68.2 | 68.3 |
| Correlation coefficient | — | 0.989 | 0.989 |
| Slope | — | 0.891 | 0.935 |
| Intercept | — | 4.8 | 2.8 |

Unit: mg/dL

The results measured by using the second reagent containing the organic silicon compound of the present invention exhibited improved slope and intercept as compared with the results measured by using the second reagent not containing the organic silicon compound of the present invention. This indicates that the organic silicon compound of the present invention established specific conditions under which the reaction between cholesterols in HDL and enzymes is predominant over the reaction between cholesterols in LDL and enzymes, whereby the characteristics of the surfactant having lipoprotein selectivity was further improved.

Example 3

Figure 2:
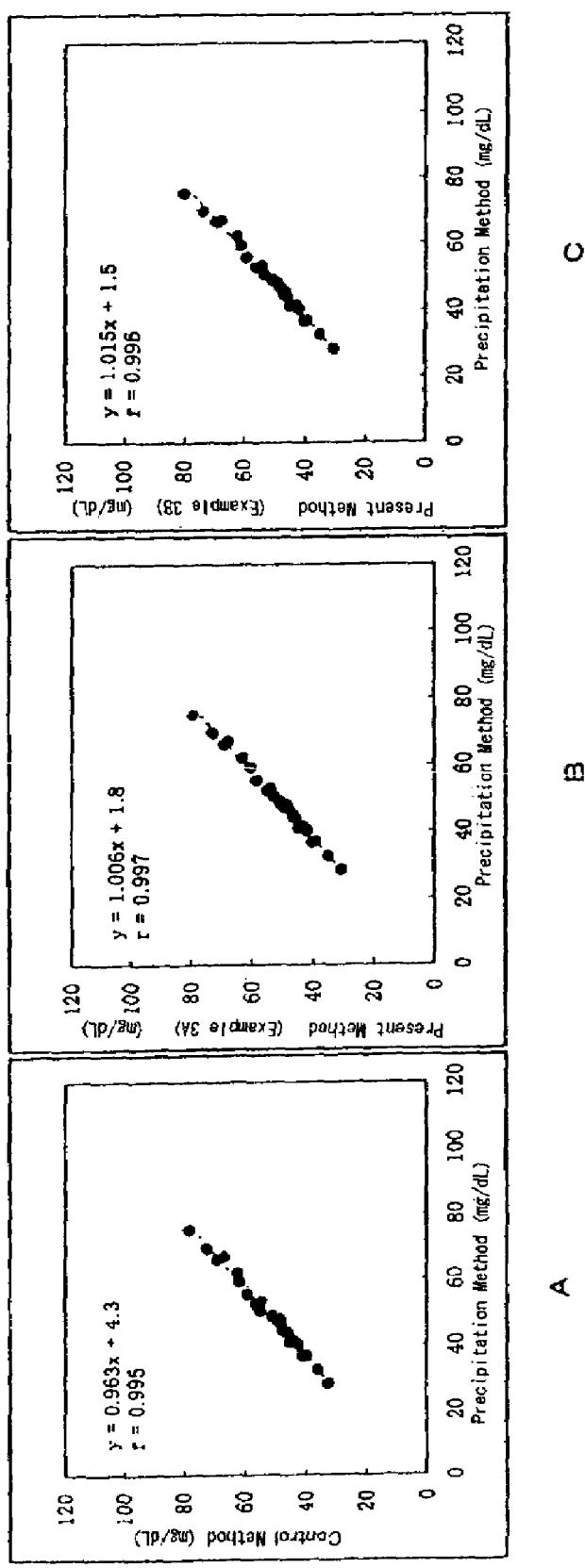
FIG. 2 is a chart for showing the correlation between the results of assaying HDL cholesterol in a blood serum sample obtained by the method of the present invention shown in Example 3A or 3B or the control method using a reagent not containing the organic silicon compound of the present invention and the results obtained by the precipitation method, wherein A, B, and C show the correlations for the control method, the method of Example 3A, and the method of Example 3B respectively.

The effect of the present invention was confirmed in the same condition as in Example 2 except that 26 serum samples containing lipoproteins were used as the samples and NET-SG-60A (Example 3A) or NET-SG-60C (Example 3B) (both at a concentration of 0.05%, manufactured by Nihon Surfactant Kogyo KK.) was used as the organic silicon compound of the present invention in the second reagent. The results are shown in Table 3 and FIG. 2.

TABLE 3

| Sample | Precipitation method | Control | Method of the present invention Example 3A | Method of the present invention Example 3B |
|---|---|---|---|---|
| 1 | 44.5 | 47.8 | 46.7 | 47.0 |
| 2 | 49.3 | 51.1 | 50.9 | 51.1 |
| 3 | 48.8 | 51.1 | 51.0 | 50.9 |
| 4 | 69.7 | 72.4 | 72.7 | 73.6 |
| 5 | 67.2 | 66.9 | 67.9 | 67.5 |
| 6 | 66.4 | 69.1 | 69.1 | 69.1 |

TABLE 3-continued

| Sample | Precipitation method | Control | Method of the present invention | |
|---|---|---|---|---|
| | | | Example 3A | Example 3B |
| 7 | 40.3 | 42.2 | 42.2 | 42.2 |
| 8 | 28.6 | 32.4 | 30.8 | 30.5 |
| 9 | 45.3 | 47.9 | 46.6 | 46.6 |
| 10 | 46.8 | 48.2 | 48.1 | 48.2 |
| 11 | 41.7 | 44.1 | 43.3 | 43.0 |
| 12 | 41.1 | 45.0 | 42.7 | 43.6 |
| 13 | 55.6 | 59.2 | 58.6 | 59.2 |
| 14 | 52.6 | 56.2 | 55.3 | 56.1 |
| 15 | 62.2 | 62.2 | 63.0 | 62.3 |
| 16 | 32.7 | 35.9 | 34.8 | 35.0 |
| 17 | 48.2 | 48.3 | 48.5 | 49.2 |
| 18 | 47.4 | 49.2 | 49.6 | 49.0 |
| 19 | 41.1 | 45.1 | 45.0 | 45.0 |
| 20 | 53.3 | 54.8 | 54.2 | 54.3 |
| 21 | 44.0 | 46.0 | 45.8 | 45.9 |
| 22 | 75.3 | 78.2 | 79.5 | 80.1 |
| 23 | 59.4 | 61.7 | 60.5 | 61.2 |
| 24 | 37.1 | 39.7 | 39.3 | 39.6 |
| 25 | 50.6 | 55.0 | 53.0 | 53.5 |
| 26 | 36.9 | 40.9 | 40.4 | 40.3 |
| Correlation coefficient | — | 0.995 | 0.997 | 0.996 |
| Slope | — | 0.963 | 1.006 | 1.015 |
| Intercept | — | 4.3 | 1.8 | 1.5 |

Unit: mg/dL

The results measured by using the second reagent containing the organic silicon compound of the present invention exhibited improved slope and intercept as compared with the results measured by using the second reagent not containing the organic silicon compound of the present invention. This indicates that the organic silicon compound of the present invention established specific conditions under which the reaction between cholesterols in HDL and enzymes is predominant over the reaction between cholesterols in LDL and enzymes, whereby the characteristics of the surfactant having lipoprotein selectivity was further improved.

Example 4

Figure 3:
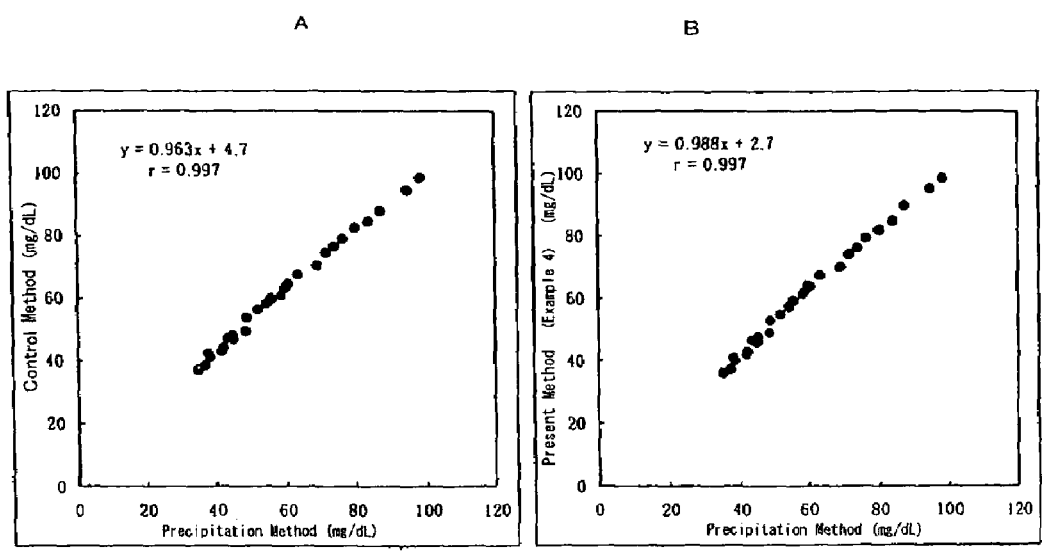
FIG. 3 is a chart for showing the correlation between the results of assaying HDL cholesterol in a blood serum sample obtained by the method of the present invention shown in Example 4 or the control method using a reagent not containing an organic silicon compound of the present invention and the results obtained by the precipitation method, wherein A shows the correlation for the control method and B shows the correlation for the method of the present invention.

The effect of the present invention was confirmed in the same condition as in Example 2 except that 30 serum samples containing lipoproteins were used as the samples and KF-700 (0.08%, manufactured by Shin-Etsu Chemical Co., Ltd.) was used as the organic silicon compound of the present invention in the second reagent. The results are shown in Table 4 and FIG. 3.

TABLE 4

| Sample | Precipitation method | Control | Method of the present invention |
|---|---|---|---|
| 1 | 98.6 | 98.7 | 98.2 |
| 2 | 95.0 | 94.5 | 95.0 |
| 3 | 87.4 | 87.9 | 89.4 |
| 4 | 84.0 | 84.7 | 84.5 |
| 5 | 80.4 | 82.6 | 81.8 |
| 6 | 76.6 | 79.0 | 79.2 |
| 7 | 74.2 | 76.6 | 76.1 |
| 8 | 71.8 | 74.6 | 74.1 |
| 9 | 69.2 | 70.6 | 70.0 |
| 10 | 63.6 | 67.6 | 67.4 |
| 11 | 60.0 | 63.8 | 64.2 |
| 12 | 60.8 | 64.7 | 63.9 |
| 13 | 59.8 | 63.2 | 62.9 |
| 14 | 58.6 | 60.9 | 61.3 |
| 15 | 55.8 | 59.7 | 59.2 |
| 16 | 55.8 | 60.0 | 59.1 |
| 17 | 54.4 | 58.3 | 57.1 |
| 18 | 52.0 | 56.3 | 54.6 |
| 19 | 49.0 | 53.8 | 52.8 |
| 20 | 48.6 | 49.5 | 48.8 |
| 21 | 45.0 | 48.2 | 47.5 |
| 22 | 43.4 | 47.1 | 46.6 |
| 23 | 45.0 | 46.8 | 46.0 |
| 24 | 44.6 | 47.0 | 45.8 |
| 25 | 42.0 | 44.0 | 42.9 |
| 26 | 41.8 | 43.0 | 42.0 |
| 27 | 38.0 | 42.3 | 40.9 |
| 28 | 38.4 | 41.1 | 39.9 |
| 29 | 37.0 | 38.5 | 37.2 |
| 30 | 35.0 | 37.0 | 36.0 |
| Correlation coefficient | — | 0.997 | 0.997 |
| Slope | — | 0.963 | 0.988 |
| Intercept | — | 4.7 | 2.7 |

The results measured by using the second reagent containing the organic silicon compound of the present invention exhibited improved slope and intercept as compared with the results measured by using the second reagent not containing the organic silicon compound of the present invention. This indicates that the organic silicon compound of the present invention established specific conditions under which the reaction between cholesterols in HDL and enzymes is predominant over the reaction between cholesterols in LDL and enzymes, whereby the characteristics of the surfactant having lipoprotein selectivity was further improved.

Example 5

The effect of the present invention was confirmed in the same condition as in Example 2 except that 20 serum samples containing lipoproteins were used as the samples and the organic silicon compounds shown in Table 5 were used in the second reagent. In Table 5, the organic silicon compounds of Examples 5A–5D were used for formulating the second reagent after dissolving these compounds in ethanol to a concentration of 10%. The organic silicon compounds of Examples 5E and 5F were used for formulating the second reagent after dissolving and mixing these compounds in ethanol together with SH8400 (modified silicone oil manufactured by Dow Corning Toray Silicone Co., Ltd.) to a respective concentration of 10%. The results are shown in Table 6.

TABLE 5

| Example | Organic silicon compound* |
|---|---|
| 5A | BY11-030 (0.03%) |
| 5B | BY22-008M (0.05%) |
| 5C | SH-244 (0.03%) |
| 5D | SH-245 (0.05%) |
| 5E | DC345 (0.02%) |
| 5F | SH200C-2cs (0.02%) |

*All manufactured by Dow Corning Toray Silicone Co., Ltd.

TABLE 6

| Sample | Precipitation method | Control | Method of the present invention ||||||
|---|---|---|---|---|---|---|---|---|
| | | | Example 5A | Example 5B | Example 5C | Example 5D | Example 5E | Example 5F |
| 1 | 90.4 | 92.0 | 93.0 | 94.5 | 93.2 | 94.7 | 93.0 | 92.7 |
| 2 | 81.4 | 83.1 | 83.1 | 84.3 | 82.8 | 82.8 | 85.9 | 83.5 |
| 3 | 77.9 | 81.5 | 82.6 | 82.0 | 82.2 | 82.6 | 82.8 | 82.9 |
| 4 | 74.4 | 77.9 | 78.2 | 79.2 | 78.5 | 79.2 | 78.5 | 78.0 |
| 5 | 72.0 | 72.9 | 74.0 | 76.0 | 73.1 | 74.2 | 75.0 | 74.2 |
| 6 | 69.9 | 70.8 | 71.1 | 71.4 | 71.1 | 71.9 | 71.4 | 70.7 |
| 7 | 68.0 | 67.2 | 68.8 | 69.3 | 68.6 | 69.2 | 69.6 | 68.4 |
| 8 | 65.4 | 70.4 | 70.3 | 71.0 | 69.6 | 71.8 | 70.5 | 69.9 |
| 9 | 65.3 | 66.7 | 66.8 | 67.1 | 66.1 | 67.9 | 68.2 | 67.2 |
| 10 | 59.9 | 62.8 | 62.4 | 63.3 | 62.7 | 63.6 | 62.6 | 62.0 |
| 11 | 58.7 | 60.7 | 60.6 | 60.9 | 61.3 | 61.7 | 60.7 | 60.4 |
| 12 | 57.9 | 61.2 | 61.6 | 62.1 | 61.2 | 61.6 | 62.0 | 61.6 |
| 13 | 56.2 | 58.5 | 57.1 | 57.8 | 57.6 | 59.1 | 58.6 | 57.4 |
| 14 | 54.0 | 55.6 | 55.6 | 57.3 | 56.3 | 55.7 | 56.7 | 55.6 |
| 15 | 52.7 | 55.3 | 55.4 | 55.5 | 54.9 | 55.7 | 55.6 | 55.3 |
| 16 | 51.8 | 52.1 | 52.4 | 52.7 | 52.6 | 53.2 | 53.1 | 52.4 |
| 17 | 50.0 | 51.1 | 52.1 | 52.4 | 50.5 | 52.0 | 51.7 | 52.1 |
| 18 | 49.4 | 52.3 | 52.5 | 51.9 | 51.7 | 52.3 | 52.0 | 52.3 |
| 19 | 43.0 | 46.1 | 44.7 | 44.9 | 45.5 | 45.4 | 44.8 | 44.2 |
| 20 | 41.1 | 43.9 | 43.2 | 44.0 | 43.4 | 43.7 | 43.8 | 43.5 |
| Correlation coefficient | — | 0.995 | 0.996 | 0.996 | 0.996 | 0.996 | 0.997 | 0.996 |
| Slope | — | 0.989 | 1.021 | 1.038 | 1.017 | 1.029 | 1.037 | 1.023 |
| Intercept | — | 2.81 | 0.99 | 0.54 | 1.15 | 1.15 | 0.56 | 0.82 |

Unit: mg/dL

The results measured by using the second reagent containing the organic silicon compound of the present invention exhibited particularly improved intercept as compared with the results measured by using the second reagent not containing the organic silicon compound of the present invention. This indicates that the organic silicon compound of the present invention established specific conditions under which the reaction with cholesterols in HDL is predominant over the reaction between cholesterols in LDL and enzymes, whereby the characteristics of the surfactant having lipoprotein selectivity was further improved.

INDUSTRIAL APPLICABILITY

Lipids in specific fractions (e.g. cholesterols) can be quantitatively determined efficiently by a simple procedure without requiring a pretreatment such as centrifugation by using the method of the present invention. In addition, because the method allows specific determination by a simple method using a small amount of sample, the method can be applied to various types of automatic analyzers. The method is thus extremely useful in the field of clinical diagnosis. The high lipoprotein selectivity particularly improves the intercept and slope, providing an advantage of minute lipoprotein selectivity control.

What is claimed is:

1. A reagent for assaying HDL-cholesterol comprising: (1) water soluble organic silicon compound or emulsified water-insoluble organic silicon compound, (2) cholesterol esterase, (3) cholesterol oxidase, (4) peroxidase, and (5) chromogen.

2. A reagent for assaying HDL-cholesterol comprising: (1) organic silicon compound, (2) cholesterol esterase, (3) cholesterol oxidase, (4) peroxidase, (5) chromogen and (6) a surfactant having lipoprotein selectivity.

3. A kit for assaying LDL-cholesterol comprising:
   a first reagent which comprises (1) organic silicon compound, (2) cholesterol esterase, (3) cholesterol oxidase, (4) peroxidase, and (5) one of two compounds generating a color by combination, and
   a second reagent which comprises (6) the other of the two compounds generating a color by combination and (7) surfactant with low lipoprotein selectivity.

4. The kit for assaying LDL-cholesterol according to claim 3, wherein the first reagent further comprises a surfactant having lipoprotein selectivity.

* * * * *